United States Patent
Hall et al.

(10) Patent No.: US 6,602,920 B2
(45) Date of Patent: *Aug. 5, 2003

(54) METHOD FOR CONVERTING NATURAL GAS TO LIQUID HYDROCARBONS

(75) Inventors: Kenneth R. Hall, College Station, TX (US); Jerry A. Bullin, Bryan, TX (US); Philip T. Eubank, Bryan, TX (US); Aydin Akgerman, College Station, TX (US); Rayford G. Anthony, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/803,122

(22) Filed: Mar. 9, 2001

(65) Prior Publication Data

US 2002/0000085 A1 Jan. 3, 2002

Related U.S. Application Data

(63) Continuation-in-part of application No. 09/574,510, filed on May 19, 2000, now Pat. No. 6,323,247, which is a continuation of application No. 09/199,502, filed on Nov. 25, 1998, now Pat. No. 6,130,260.

(51) Int. Cl.[7] .......................... C07C 27/00; C07C 2/00; C07C 11/00; C07C 2/56
(52) U.S. Cl. .................. 518/700; 518/703; 585/534; 585/535; 585/540; 585/541; 585/709
(58) Field of Search ............... 518/700, 703; 585/534, 535, 540, 541, 709

(56) References Cited

U.S. PATENT DOCUMENTS

| 1,023,783 | A | 4/1912 | Knapp |
|---|---|---|---|
| 1,229,886 | A | 6/1917 | Cherry |
| 1,773,611 | A | 8/1930 | Banck |
| 1,800,586 | A | 4/1931 | Youker |
| 1,880,307 | A | 10/1932 | Wulff |
| 1,904,426 | A | 4/1933 | Eisenhut |
| 1,917,627 | A | 7/1933 | Wulff |
| 1,966,779 | A | 7/1934 | Wulff ........................ 260/170 |
| RE19,500 | E | 3/1935 | Youker ........................ 196/10 |
| RE19,794 | E | 12/1935 | Banck et al. ................ 260/170 |
| 2,028,014 | A | 1/1936 | Reinecke ..................... 204/31 |
| 2,037,056 | A | 4/1936 | Wulff ......................... 260/170 |
| 2,080,931 | A | 5/1937 | Rose ........................... 204/31 |
| 2,160,170 | A | 5/1939 | Martin et al. ............... 260/679 |
| 2,328,864 | A | 9/1943 | Throckmorton ............. 196/10 |
| 2,475,282 | A | 7/1949 | Hasche ...................... 23/209.4 |
| 2,550,089 | A | 4/1951 | Schlesman .................. 204/171 |
| 2,558,861 | A | 7/1951 | Liggett ........................ 23/288 |

(List continued on next page.)

FOREIGN PATENT DOCUMENTS

| EP | 0289391 | 3/1990 | ............ C07C/2/76 |
|---|---|---|---|
| EP | 0435591 A2 | 12/1990 | ........... C07C/11/24 |

OTHER PUBLICATIONS

A. Malek, et al., "Hydrogen Purification from Refinery Fuel Gas by Pressure Swing Adsorption." AIChE Journal vol.44, No. 9, Sep. 1998, pp. 1985–1992.

Marshall Sittig, "Acetylene processes and Products." Chemical Process Review No. 22, 1968, 229 pages..

(List continued on next page.)

Primary Examiner—J. Parsa
(74) Attorney, Agent, or Firm—Baker Botts L.L.P.

(57) ABSTRACT

A process for converting natural gas to a liquid includes heating the gas to a selected range of temperature to convert a fraction of the gas stream to reactive hydrocarbons, primarily ethylene or acetylene, and reacting methane and the reactive hydrocarbons in the presence of an acidic catalyst to produce a liquid, predominantly naphtha or gasoline. A portion of the incoming natural gas may be used to heat the remainder of the natural gas to the selected range of temperature. Hydrogen resulting from the reactions may be used to make electricity in a fuel cell. Alternatively, hydrogen may be burned to heat the natural gas to the selected range of temperature.

54 Claims, 6 Drawing Sheets

U.S. PATENT DOCUMENTS

| | | | |
|---|---|---|---|
| 2,645,673 A | 7/1953 | Hasche | 260/679 |
| 2,675,294 A | 4/1954 | Keith | 23/1 |
| 2,714,126 A | 7/1955 | Keith | 260/679 |
| 2,751,424 A | 6/1956 | Hasche | 260/679 |
| 2,768,223 A | 10/1956 | Williams et al. | 260/679 |
| 2,986,505 A | 5/1961 | Lauer et al. | 204/156 |
| 3,156,733 A | 11/1964 | Happel et al. | 260/679 |
| 3,168,592 A | 2/1965 | Cichelli et al. | 260/679 |
| 3,262,757 A | 7/1966 | Bodmer | 23/284 |
| 3,283,028 A | 11/1966 | Bergstrom et al. | 260/683 |
| 3,320,146 A | 5/1967 | Neely, Jr. | 204/171 |
| 3,389,189 A | 6/1968 | Hirayama et al. | 260/679 |
| 3,409,695 A | 11/1968 | Sennewald et al. | 260/679 |
| 3,622,493 A | 11/1971 | Crusco | 204/323 |
| 3,663,394 A | 5/1972 | Kawahara | 204/168 |
| 3,674,668 A | 7/1972 | Bjornson et al. | 204/171 |
| 3,697,612 A | 10/1972 | Maniero et al. | 260/679 |
| 3,703,460 A | 11/1972 | Shair et al. | 204/327 |
| 4,014,947 A | 3/1977 | Kowgly et al. | |
| 4,128,595 A | 12/1978 | Montgomery | 585/261 |
| 4,309,359 A | 1/1982 | Pinto | 518/705 |
| 4,336,045 A | 6/1982 | Saunders et al. | |
| 4,367,363 A | 1/1983 | Katz et al. | 585/809 |
| 4,378,232 A | 3/1983 | Peuckert et al. | 48/210 |
| 4,424,401 A | 1/1984 | White et al. | 585/416 |
| 4,492,591 A | 1/1985 | O'Reilly | 62/632 |
| 4,497,970 A | 2/1985 | Young | 585/417 |
| 4,513,164 A | 4/1985 | Olah | 585/700 |
| 4,566,961 A | 1/1986 | Diaz et al. | 204/168 |
| 4,575,383 A | 3/1986 | Lowther et al. | 48/212 |
| 4,588,850 A | 5/1986 | Mueller et al. | 585/539 |
| 4,704,496 A | 11/1987 | Paparizos et al. | 585/500 |
| 4,705,906 A | 11/1987 | Brophy et al. | 585/262 |
| 4,705,908 A | 11/1987 | Gondouin | 585/500 |
| 4,757,787 A | 7/1988 | Risitano et al. | 123/25 A |
| 4,761,515 A | 8/1988 | Gondouin | 585/500 |
| 4,795,536 A | 1/1989 | Young et al. | 424/422 |
| 4,797,185 A | 1/1989 | Polak et al. | 205/637 |
| 4,822,940 A | 4/1989 | Leff et al. | 585/415 |
| 4,906,800 A | 3/1990 | Henry et al. | 585/260 |
| 4,950,821 A | 8/1990 | Ratnasamy et al. | 585/310 |
| 4,952,743 A | 8/1990 | Come | 585/500 |
| 4,973,776 A | 11/1990 | Allenger et al. | 585/310 |
| 4,973,786 A | 11/1990 | Karra | 585/500 |
| 4,981,829 A | 1/1991 | Shutt et al. | 502/202 |
| 5,012,029 A | 4/1991 | Han et al. | 585/500 |
| 5,015,349 A | 5/1991 | Suib et al. | 204/168 |
| 5,019,355 A | 5/1991 | Sackinger | 422/186.04 |
| 5,026,944 A | 6/1991 | Allenger et al. | 585/500 |
| 5,053,575 A | 10/1991 | Nikravech et al. | 585/500 |
| 5,073,666 A | 12/1991 | Zemanian et al. | 585/734 |
| 5,118,893 A | 6/1992 | Timmons et al. | 585/416 |
| 5,131,993 A | 7/1992 | Suib et al. | 204/168 |
| 5,138,113 A | 8/1992 | Juguin et al. | 585/322 |
| 5,181,998 A | 1/1993 | Murphy et al. | 204/157.15 |
| 5,205,912 A | 4/1993 | Murphy | 204/157.15 |
| 5,205,915 A | 4/1993 | Ravella et al. | 204/157.15 |
| 5,277,773 A | 1/1994 | Murphy | 204/168 |
| 5,328,577 A | 7/1994 | Murphy | 204/168 |
| 5,336,825 A | 8/1994 | Choudhary et al. | 585/500 |
| 5,472,581 A | 12/1995 | Wan | 204/157.6 |
| 5,498,278 A | 3/1996 | Edlund | 96/11 |
| 5,510,550 A | 4/1996 | Cheung et al. | 585/259 |
| 5,518,530 A | 5/1996 | Sakai et al. | 96/11 |
| 5,583,274 A | 12/1996 | Cheung et al. | 585/261 |
| 5,585,318 A | 12/1996 | Johnson et al. | 502/330 |
| 5,587,348 A | 12/1996 | Brown et al. | 502/230 |
| 5,629,102 A | 5/1997 | Werth | 429/17 |
| 5,675,041 A | 10/1997 | Kiss et al. | 568/454 |
| 5,695,618 A | 12/1997 | O'Young et al. | 204/157.43 |
| 5,714,657 A | 2/1998 | de Vries | 585/310 |
| 5,749,937 A | 5/1998 | Detering et al. | 75/10.19 |
| 6,130,260 A * | 10/2000 | Hall et al. | 518/703 |
| 6,323,247 B1 * | 11/2001 | Hall et al. | 518/700 |

OTHER PUBLICATIONS

L. Bromberg, et al., "Plasma Reforming of Methane." Energy & Fuels Vo. 12, No. 1, 1998, pp. 11–18.

Michael j. Corke "GTL Technologies Focus on Lowering Cost." Oil & Gas Journal, Sep. 21, 1998, pp. 71–77.

Michael J. Corke, "Economics Favor GTL Projects with Condensate Coproduction." Oil & Gas Journal Sep. 28, 1998, pp. 96–101.

Alan H. Singleton, "Advances Make gas–to–liquids Process Competitive for Romote Locations." Oil & Gas Journal Aug. 4, 1997, pp. 68–72.

T. Kodama, et al., "High–Temperature Conversion of CH4 to C2–Hydrocarbons and H2 Using a Redox System of Metal Oxide." Energy & Fuels, vol. 11, No. 6 1997, pp. 1257–1263.

S. H. Bauer, et al., "Upgrading of Methane under Homogeneous Thermal Conditions: An Environmental and Economic Imperative." Energy & Fuels, vol. 11, 1997, pp. 1204–1218.

"A—Liquefied Natural Gas as a Heavy Vehicle Fuel." Commerce Business Daily, Jul. 17, 1997.

Lance L. Lobban, et al., "Oxidative Coupling of Methane Using an AC Electric Discharge." American Institute of Chemical Engineers 1996 Annual Meeting, Session 37, Paper 37f.

D. Q. kern, "Process Heat Transfer." McGraw–Hill Book Co., New Yorrk (1950).

PCT International Search Report Application No. PCT/US 02/07183, Oct. 2, 2002.

* cited by examiner

METHOD FOR CONVERTING NATURAL GAS TO LIQUID HYDROCARBONS

This is a continuation in part of a application Ser. No. 09/574,510 filed May 19, 2000, issued as U.S. Pat. No. 6,323,247 which is a continuation Ser. No. 09/199,502 of U.S. Pat. No. 6,130,260, filed on Nov. 25, 1998.

FIELD OF THE INVENTION

This invention pertains to conversion of natural gas to hydrocarbon liquids. More particularly, natural gas is converted to reactive hydrocarbons and the reactive hydrocarbons are reacted with additional natural gas to form hydrocarbon liquids.

BACKGROUND OF THE INVENTION

Natural gas often contains about 60–100 mole per cent methane, the balance being primarily heavier alkanes. Alkanes of increasing carbon number are normally present in decreasing amounts. Carbon dioxide, nitrogen, and other gases may be present.

Conversion of natural gas into hydrocarbon liquids has been a technological goal for many years. The goal has become even more important in recent years as more natural gas has been found in remote locations, where gas pipelines may not be economically justified. A significant portion of the world reserves of natural gas occurs in such remote regions. While liquefied natural gas (LNG) and methanol projects have long attracted attention by making possible conversion of natural gas to a liquid, in recent years the advent of large scale projects based upon Fisher-Tropsch (F-T) technology have attracted more attention. A review of proposed and existing F-T projects along with a discussion of economics of the projects has recently been published (*Oil and Gas J.*, Sep. 21 and Sep. 28, 1998). In this technology, natural gas is first converted to "syngas," which is a mixture of carbon monoxide and hydrogen, and the syngas is converted to liquid paraffinic and olefinic hydrocarbons of varying chain lengths. The F-T technology was developed for using coal as a feed stock, and only two plants now operate using natural gas as feedstock—in South Africa and in Malaysia. A study showed that for a plant producing 45,000 bbls/day (BPD) of liquids in a U.S. location in 1993, investment costs would have been about $38,000 per BPD production (*Oil and Gas J.*, Sep. 28, 1998, p. 99). Improved designs are said to lower investment cost to the range of $30,000 per BPD for a 20,000 BPD facility. Such a plant would use about 180 MMSCFD of natural gas, 10 million GPD of raw water and 150 BPD of normal butane, and would produce excess steam, which could be used to produce 10 megawatts of electricity.

The conversion of natural gas to unsaturated hydrocarbons and hydrogen by subjecting the hydrocarbons in natural gas to high temperatures produced by electromagnetic radiation or electrical discharges has been extensively studied. U.S. Pat. No. 5,277,773 discloses a conversion process that subjects methane plus hydrocarbons to microwave radiation so as to produce an electric discharge in an electromagnetic field. U.S. Pat. No. 5,131,993 discloses a method for cracking a hydrocarbon material in the presence of a microwave discharge plasma and a carrier gas, such as oxygen, hydrogen and nitrogen, and, generally, a catalyst. U.S. Pat. No. 3,389,189 is an example of patents relating to production of acetylene by an electric arc.

Methane pyrolysis to acetylene and hydrogen by rapid heating in a reaction zone and subsequent rapid quenching has also been extensively investigated. Subatmospheric pressures and specific ranges of velocities of hydrocarbon gases through the reaction zone are disclosed in U.S. Pat. No. 3,156,733. Heat is supplied by burning of hydrocarbons.

Although the prior art has disclosed a range of methods for forming acetylene or ethylene from natural gas, an energy-efficient process for converting natural gas to a liquid that can be transported efficiently from remote areas to market areas has not been available. What is needed is a process that does not require large capital and operating expenditures such as required by the prior art processes. Also, the process should be energy efficient.

SUMMARY OF THE INVENTION

A process for conversion of natural gas to a hydrocarbon liquid for transport from remote locations is provided. In one embodiment, the natural gas is heated to a temperature at which a fraction of the natural gas is converted to hydrogen and a reactive hydrocarbon such as acetylene or ethylene. The stream is then quenched to stop any further reactions and then reacted in the presence of a catalyst to form the liquid to be transported, predominantly naphtha or gasoline. Hydrogen may be separated after quenching and before the catalytic reactor. Heat for raising the temperature of the natural gas stream is provided by burning of a portion of the natural gas feed stream. Hydrogen produced in the reaction is available for further refining or in generation of electricity by oxidation in a fuel cell or turbine. In another embodiment, heat produced from the fuel cell is used to generate additional electricity. In another embodiment, the acetylene portion of the reactive hydrocarbon is reacted with hydrogen to form ethylene prior to reacting to form the liquid to be transported. In another embodiment, hydrogen produced in the reaction is burned to raise the temperature of the natural gas stream and the acetylene portion of the reactive hydrocarbon is reacted with hydrogen to form ethylene prior to reacting to form the liquid to be transported. In still another embodiment, hydrogen produced in the process is used to generate electrical power, the electrical power used to heat the natural gas stream, and the acetylene portion of the reactive hydrocarbon stream is reacted with hydrogen to form ethylene prior to reacting to form the liquid to be transported.

DESCRIPTION OF PREFERRED EMBODIMENTS

Figure 1:
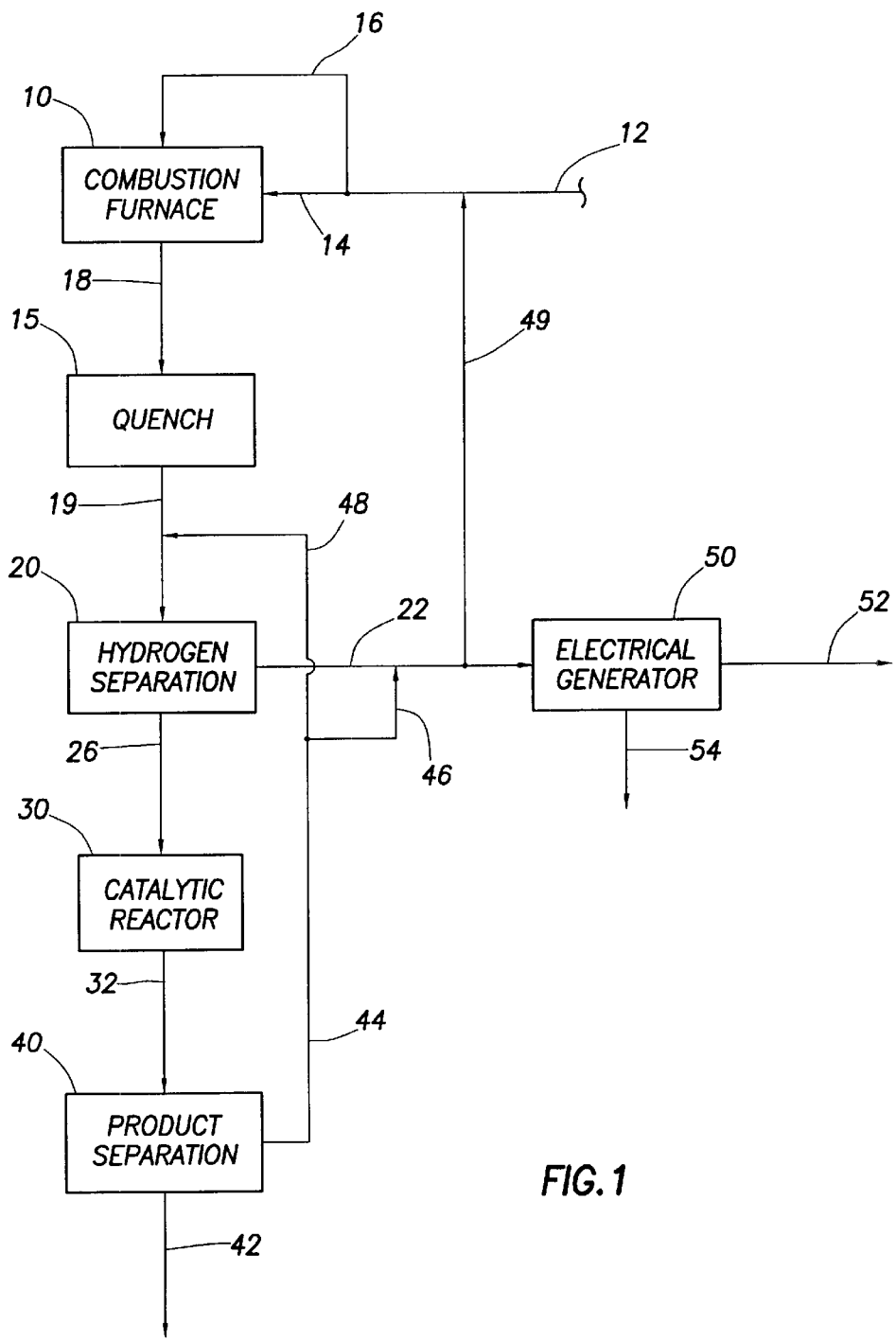
FIG. 1 shows a process diagram for one embodiment of the process of this invention in which the natural gas is heated to reaction temperature by burning a portion of the natural gas in a furnace.

U.S. Pat. No. 6,130,260 and application Ser. No. 09/574,510 filed May 19, 2000, are incorporated by reference herein. FIG. 1 shows one embodiment of the steps for producing a liquid product such as naphtha or gasoline from natural gas in the present invention. In this embodiment, a portion of the natural gas feed is diverted from the feed stream to the burners in the combustion furnace 10, where the diverted natural gas is burned, preferably with oxygen-enriched, air such that NOx production from combustion furnace 10 is decreased. As shown in FIG. 1, inlet gas stream 12 is separated into inlet gas feed stream 14 and inlet gas burn stream 16. Inlet gas feed stream 14 is conveyed to the reaction chamber of combustion furnace 10. Inlet gas burn stream 16 is conveyed to the combustion chamber of combustion furnace 10. Inlet gas feed stream 14 is preferably pre-heated in pre-heaters (not shown) before it is heated to the preferred reaction temperature by heat exchange with the hydrocarbon-combustion gas. The flame temperature of inlet gas burn stream 16 should be adequate to reach a desired reaction temperature preferably between 1000 and 1800 K without oxygen enrichment of air, but sufficient enrichment can be easily achieved with membrane units, which are well known in the art, and this will avoid the necessity of NOx control in emissions from combustion furnace 10. Addition of water to the combustion zone of combustion furnace 10 may be used to lower flame temperature to a desired range, preferably about 300 to 500 K above the preferred reaction temperature of natural gas passing through tubes of combustion furnace 10. Residence time of gas in the tubes of combustion furnace 10 should be long enough to convert inlet gas feed stream 14 to acetylene, ethylene, and other reactive compounds and not so long as to allow significant further reactions before the quenching step, which is discussed below. It is preferred to maintain the residence time to under 100 milliseconds, most preferably under 80 milliseconds to minimize coke formation. Bringing the natural gas feed stream, for simplicity here considered methane only, to high temperature causes the following reaction to occur:

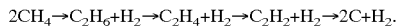

$2CH_4 \rightarrow C_2H_6+H_2 \rightarrow C_2H_4+H_2 \rightarrow C_2H_2+H_2 \rightarrow 2C+H_2$.

The desired products from this series of reactions are ethylene and acetylene. Suppression of the last reaction or last two reactions may be required to achieve the desired products. This may be accomplished by such methods as adjusting the reaction temperature and pressure, and/or quenching after a desired residence time. The desired hydrocarbon products of the reactions are designated herein as "reactive products." It is preferred to maintain the pressure of the natural gas within the reaction chamber of combustion furnace 10 to between 1 and 20 bars to achieve the reactive products. The reactive products resulting from the reaction in combustion furnace 10 leave combustion furnace 10 through furnace outlet stream 18.

Figure 3:
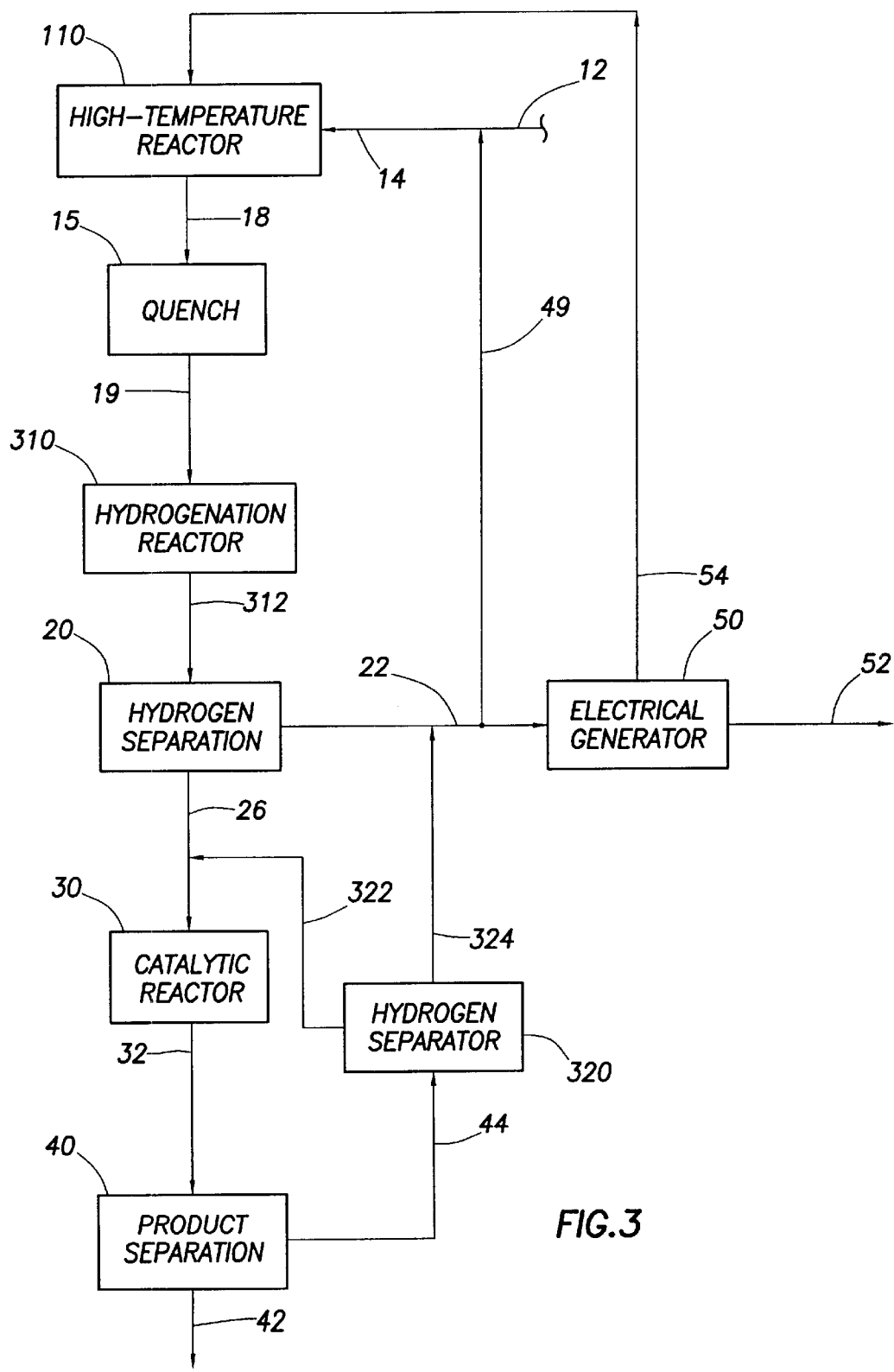
FIG. 3 shows a process diagram for one embodiment of the process of this invention in which the natural gas is heated to reaction temperature by burning of hydrogen in a furnace and acetylene is reacted to ethylene prior to liquefaction.

In an alternative embodiment, shown in FIG. 3, natural gas is heated in high-temperature reactor 110 by means of electrical power that is produced by use of hydrogen in electrical power generator 50. Inlet gas stream 12 becomes inlet gas feed stream 14 and is directed to the reaction chamber of high temperature reactor 110. The electrical power may be produced by, for example, fuel cells powered by hydrogen or by a combined cycle gas or hydrogen gas turbine driving electrical generators. Water is also produced. Investment costs for fuel cell production of electrical power are high at present, but may be reduced by improved technology in the future. Combined cycle gas turbines are well known and at present produce electrical power at significantly lower capital costs per kW (approximately $385 per kW) than the capital costs of fuel cells (estimated at $3,000 per kW). In either case, the electrical power is used to increase the temperature of the natural gas stream entering high-temperature reactor 110. The high temperature may be produced from the electrical power by an electric arc or silent discharge between electrodes, using methods well known in the art. Alternatively, the high temperature may be produced by resistance heating of electrodes. In another alternative embodiment, a plasma may be formed in the natural gas stream using a plasma reactor, such as the "Plasmatron" sold by Praxair, Thermal Spray Systems, N670 Communication Drive, Appleton, Wis. 54915. Plasma temperatures are higher than the preferred temperature range for the gas reactions of this invention, so a more energy-efficient process may be achieved without bringing the natural gas to plasma temperature. The higher temperature produces extra components in the product stream that require a great deal more energy and would make the process not as energy efficient.

In another alternative embodiment, shown in FIG. 4, hydrogen separated from the reactive products, as described below, is directed to hydrogen combustion furnace 210, where the hydrogen is burned, preferably with oxygen-enriched air such that NOx production from hydrogen combustion furnace 210 is decreased. As further shown in FIG. 4, inlet gas stream 12 becomes inlet gas feed stream 14 and is directed to reaction chamber of hydrogen combustion furnace 210. Flame temperature of hydrogen is adequate to reach a desired reaction temperature without oxygen enrichment of air, but sufficient enrichment can be easily achieved with membrane units, which are well known in the art, and this will avoid the necessity of NOx control in emissions from hydrogen combustion furnace 210. Addition of water to the combustion zone of hydrogen combustion furnace 210 may be used to lower flame temperature to a desired range, preferably about 300 to 500 K above the preferred reaction temperature of natural gas passing through tubes in hydrogen combustion furnace 210.

The materials of construction of combustion furnace 10, high temperature reactor 110, and hydrogen combustion furnace 210 are not standard. Specialty materials such as tungsten, tantalum or ceramics may be used. The temperature rise should occur in a short period of time. The furnaces may be of the double-radiant-section box-type as pictured in FIG. 19.5, p. 681, of D. Q. Kern, *Process Heat Transfer*, McGraw-Hill Book Co., New York (1950). The furnace may use tantalum (Ta) or silicon/carbide tubing. Steam pressures will be low, about 6 psig. Kinetic calculations indicate a suitable time for heating the natural gas to the reaction temperature is in the range from about 1 millisecond to about 100 milliseconds. To stop the reactions and prevent the reverse reactions or further reactions to form carbon and other hydrocarbon compounds, rapid cooling or "quenching" is essential, typically in 10 to 100 milliseconds. As shown in FIG. 1, furnace outlet stream 18 is directed to quench system 15. Quenched furnace outlet stream 18 exits quench system 15 through quench outlet stream 19. The quench in quench system 15 maybe achieved by spraying water, oil, or liquid product into furnace outlet stream 18; "dumped" into water, natural gas feed, or liquid products; or expanded in a kinetic energy quench such as a Joule-Thompson expander, choke nozzle or turbo expander. This quench occurs in a similar fashion in high-temperature reactor 110 in FIG. 3, and hydrogen combustion furnace 210 in FIG. 4.

Furnace outlet stream 18 is typically essentially one part alkene/alkyne mixture to three parts methane. In particular, "lean" natural gas, i.e., gas with 95% or greater methane reacts to mostly acetylene as a reactive product. Where the natural gas is lean, it is desirable to operate the furnace in the upper end of the desired range to achieve a higher content of alkynes, in particular acetylene. In contrast, in a richer stream, it may be desirable to operate at a temperature lower in the desirable range to achieve a higher content of alkenes, primarily ethylene.

As shown in FIG. 1 while the gas in furnace outlet stream 18 is still at a temperature above 500 K, but after quenching in quench system 15, a portion of the hydrogen in quench outlet stream 19 may be separated from the reactive hydrocarbon in hydrogen separator 20. In an alternative embodiment, all of the hydrogen is directed to liquefaction reactor 30 without the separator step of hydrogen separator 20. This separation step may be performed by any of a variety of processes, including membrane or pressure swing processes, described for example in: A. Malek and S. Farooq, "Hydrogen Purification from Refinery Fuel Gas by Pressure Swing Adsorption", *AIChE J*. 44, 1985 (1998). The hydrogen is removed from hydrogen gas separator 20 through hydrogen separator hydrogen stream 22. Hydrogen separator hydrogen stream 22 is composed primarily of hydrogen, but may also contain trace amounts of the other components in furnace outlet stream 18. After removal of the a portion of the hydrogen in hydrogen gas separator 20, the remaining portion of quench outlet stream 19 is removed from hydrogen gas separator 20 through hydrogen separator outlet stream 26.

Figure 5:
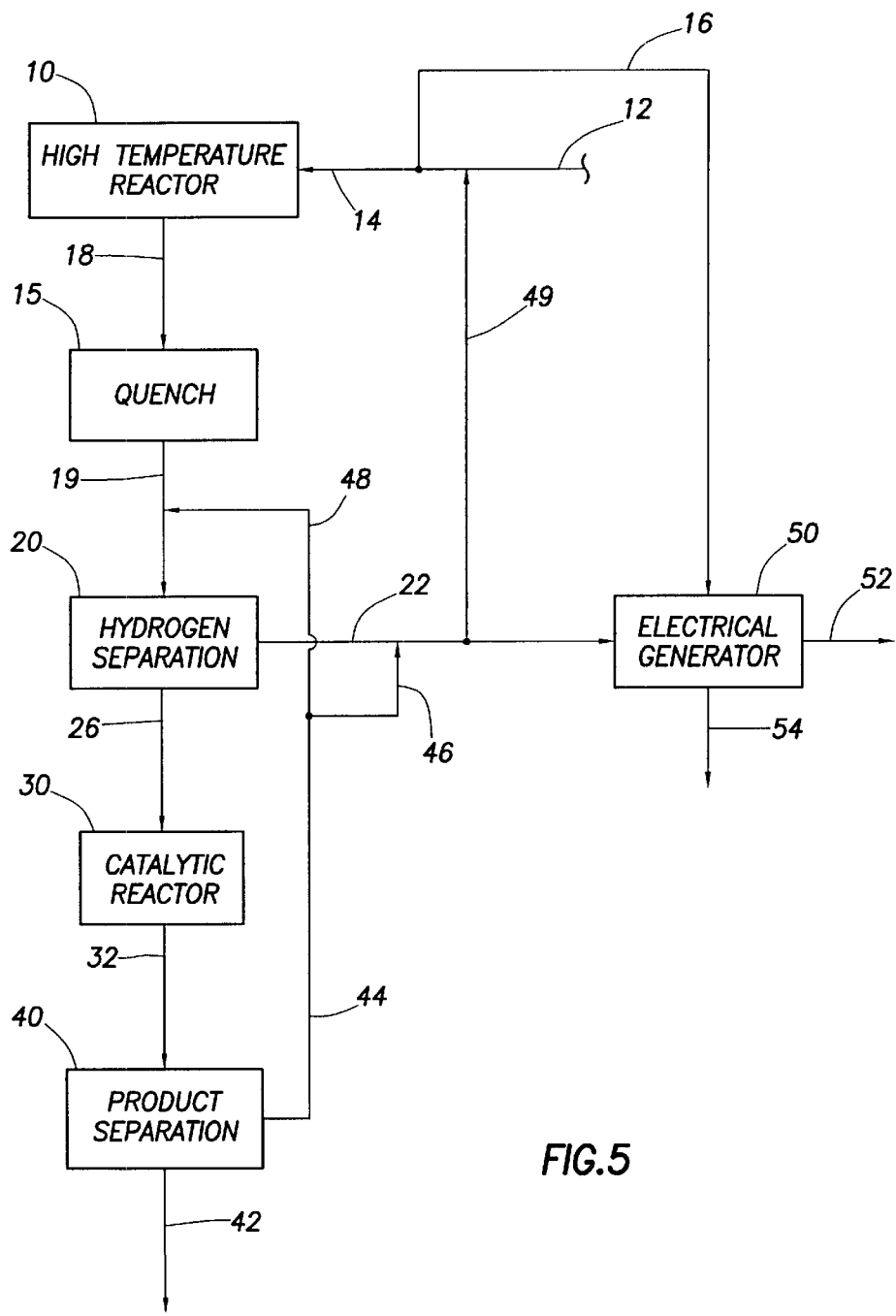
FIG. 5 shows a process diagram for one embodiment of the process of this invention in which the natural gas is heated to reaction temperature by electrical energy produced by hydrogen and a portion of the natural gas.
Figure 6:
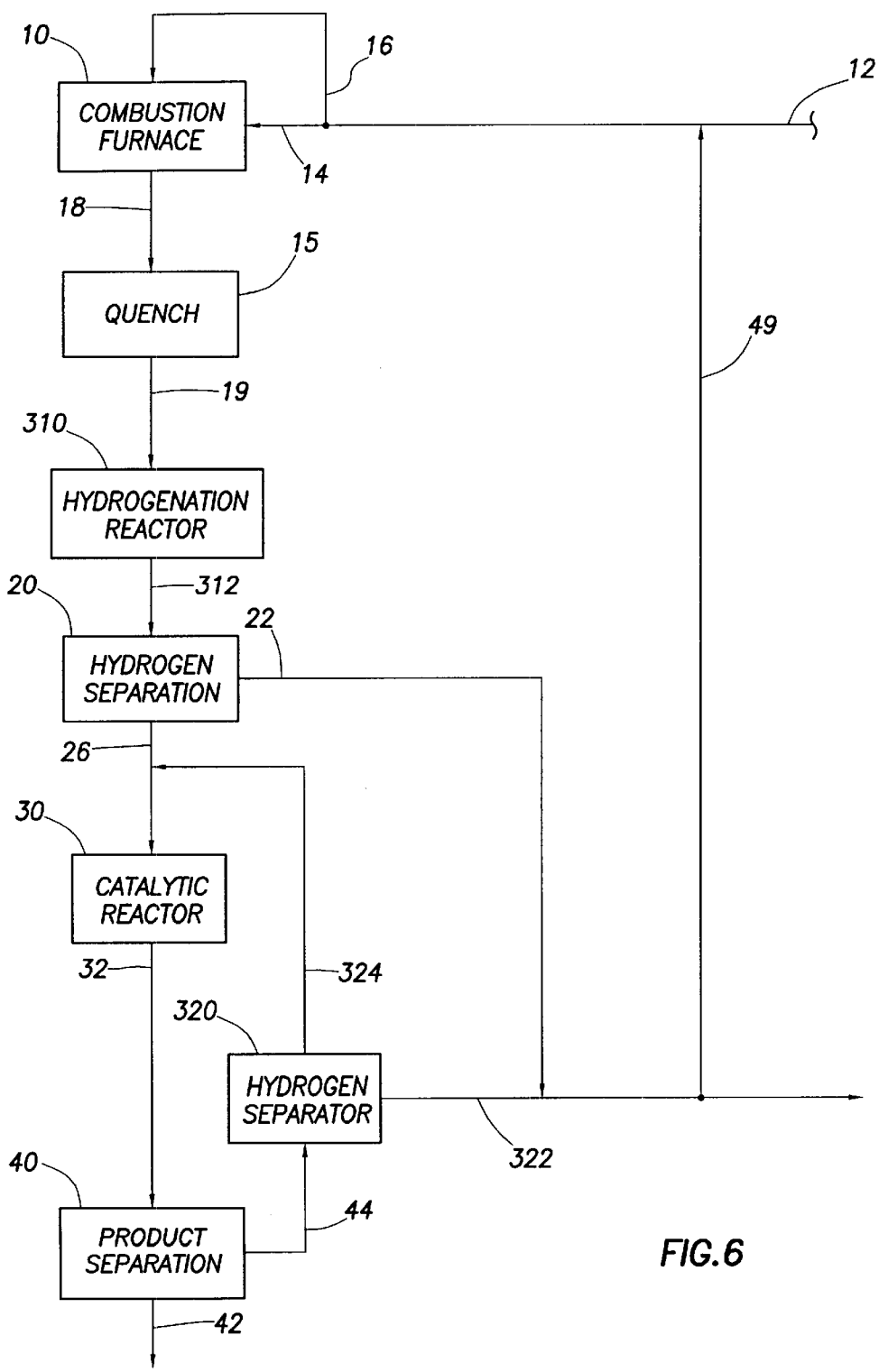
FIG. 6 shows a process diagram for one embodiment of the process of this invention in which the natural gas is heated to reaction temperature by burning a portion of the natural gas in a furnace.

As shown in FIG. 1, a portion of hydrogen separator hydrogen stream 26 may be recycled and combined with inlet gas stream 12 through recycle stream 49. Hydrogen separator hydrogen stream 22 may be used in any number of processes. In one embodiment of the present invention, as shown in FIG. 1, hydrogen separated in hydrogen separator 20 may be used to generate water and electricity by combining it with oxygen or by burning it with oxygen in a turbine in electrical generator 50. For fuel cells, any fuel cell design that uses a hydrogen stream and an oxygen stream may be used, for example polymer electrolyte, alkaline, phosphoric acid, molten carbonate, and solid oxide fuel cells. Heat generated by the fuel cell or turbine may be used to boil the water exiting the fuel cell, forming steam. This steam maybe used to generate electricity, for instance in a steam turbine. This electricity may be sold, or as shown in FIG. 3, used to power high-temperature reactor 110. The heat generated by the fuel cell or turbine may also be used in heat exchangers to raise the temperatures of streams in the process, such as in the preheaters. In an alternate embodiment, shown in FIG. 2, hydrogen separator outlet stream 22 may be produced as a product. In still another alternative embodiment, shown in FIG. 4, hydrogen separator recycle stream 22 is burned directly in hydrogen combustion furnace 210. As shown in FIG. 5, a portion of inlet gas stream 12 may be separated from inlet gas stream 12 and routed through supplemental gas stream 16 to electrical generator 50. In this way, additional electrical power may be generated. As shown in FIG. 6, electrical generator 50 may be eliminated entirely so as to maximize hydrogen production.

As further shown in FIG. 1, hydrogen separator outlet stream 26, which includes the reactive products, is conveyed from hydrogen separator 20 to liquefaction reactor 30. Liquefaction reactor 30 is a catalytic reactor that may include recycle and is designed to convert the reactive products to hydrocarbon liquids such as naphtha or gasoline. The principal liquefaction reactions in liquefaction reactor 30 are as follows:

For acetylene,

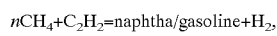
$n\text{CH}_4 + \text{C}_2\text{H}_2 = \text{naphtha/gasoline} + \text{H}_2$, and for ethylene,

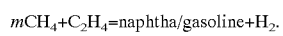
$m\text{CH}_4 + \text{C}_2\text{H}_4 = \text{naphtha/gasoline} + \text{H}_2$.

This reaction must be catalyzed to suppress the reaction of acetylene to benzene and to enhance the conversion to hydrocarbon liquids such as naphtha or gasoline, which is preferred for the method of this invention.

Liquefaction reactor 30 shown in FIG. 1, should produce predominantly naphtha or gasoline, but may also produce some aromatic and cyclic compounds. The vapor pressure of naphtha or gasoline is about 1 bar at 40° C. Thus, it can be transported via truck or ship. Heavier hydrocarbons such as crude oil may be added to the produced liquid to reduce vapor pressure of a liquid to be transported.

The reaction to produce naphtha or gasoline is thermodynamically favorable. The equilibrium thermodynamics for the reactions of acetylene and ethylene with methane are more favorable at low to moderate temperatures (300–1000 K). It is well known in the chemical industry that alkanes of ethane and higher can be converted to higher molecular weight hydrocarbons using acid catalysts, such as the zeolites H-ZSM-5 or Ultrastable Y (USY).

Applicants have discovered that the amount of Bröenstead Acid sites on the catalyst should be maximized in comparison to the Lewis acid sites. This maybe accomplished by increasing the silica to alumina ratio in the catalyst (Y Zeolites typically have Si/Al ratios of 2–8 whereas ZSM-5 typically has an Si/Al ratio of 15–30,000). Other alkylation catalysts are known in the chemical industry. In the present invention, the reaction of acetylene and ethylene to benzene is suppressed and the reaction of these reactive hydrocarbons with methane is enhanced. Steam may be introduced into the reactor to achieve the desired conversion results. The preferred reactor conditions are temperatures in the range from about 300 to about 1000 K and pressure in the range from about 2 to about 30 bar. The products of the liquefaction reaction leave liquefaction reactor 30 through catalytic reactor outlet stream 32.

As shown in FIG. 1, catalytic reactor outlet stream 32 maybe sent to product separator 40. The primary purpose of product separator 40 is to separate the desired hydrocarbon liquid products from any lighter, primarily gaseous components that may remain after liquefaction. It should be understood that a cooling step may be considered a part of product separator 40 of FIG. 1. Cooling of the stream after the reaction may be necessary, depending upon the method of final separation and the optimum conditions for that separation. If the product separator 40 is simply a gas-liquid or flash separation, cooling may be necessary. Distillation, adsorption or absorption separation processes, including pressure-swing adsorption and membrane separation, may be used for the final separation. Any known hydrocarbon liquid-gas separation processes may be used for product separator 40, which is considered a part of the catalytic reactor. The liquid hydrocarbons separated in product separator 40 are sent to storage or transport facilities through product separation outlet stream 42. The primarily gaseous components separated in product separator 40, which may consist primarily of hydrogen may be sent through light gas recycle stream 44 to electrical generator 50 through recycle purge stream 46, combined with reactor outlet stream 18 through light gas to reactor outlet stream 48, or a portion of recycle purge stream 46 may be sent to each. Alternatively, as shown in FIG. 4, light gas recycle stream 44 may be conveyed to hydrogen combustion furnace 210 for combustion rather than to a fuel cell or turbine for conversion to electricity.

Note that processing steps may be added after liquefaction and before product separator 40 or, alternatively, after product separator 40, to convert the hydrocarbon liquids such as naphtha or gasoline or to heavier compounds such as diesel.

Figure 2:
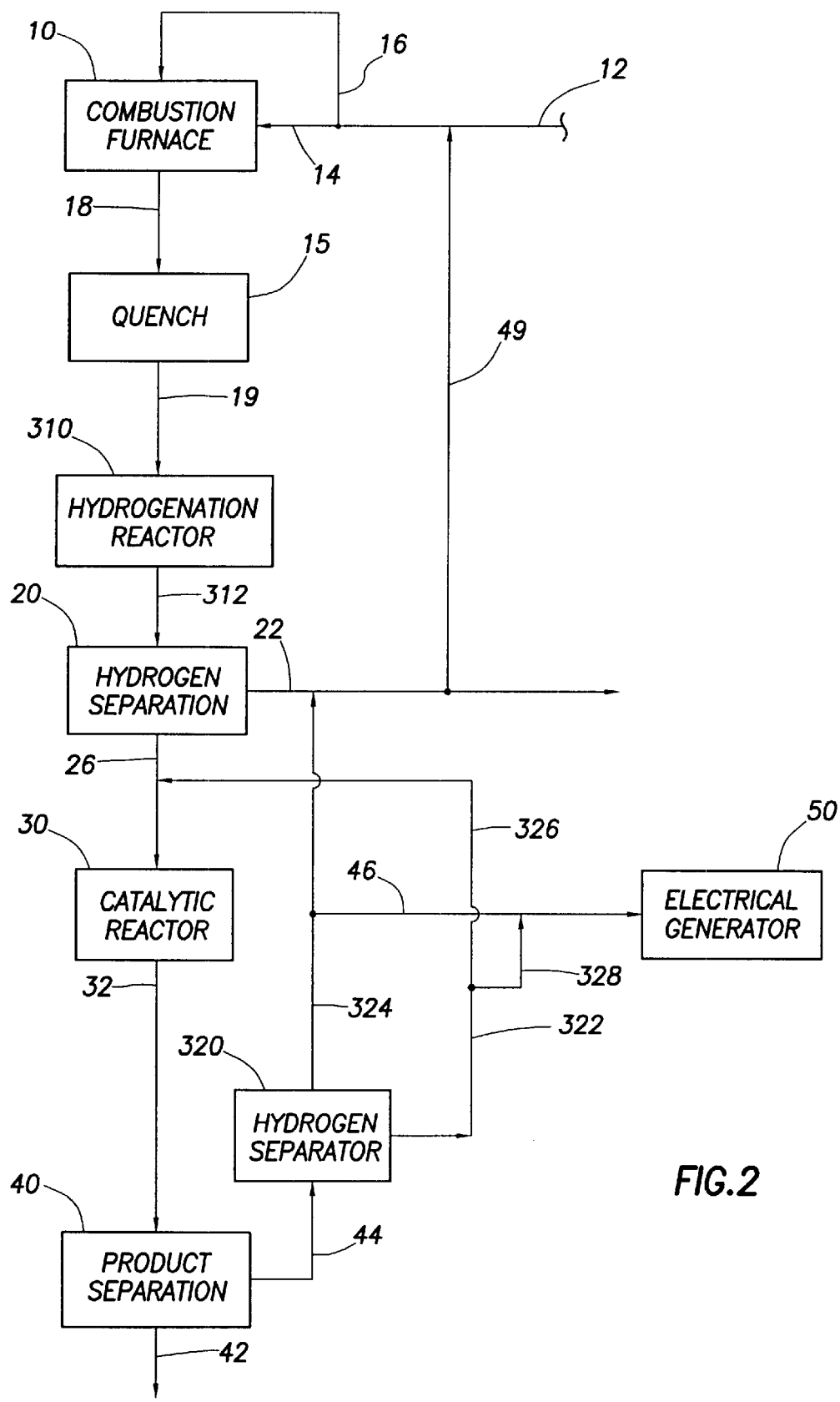
FIG. 2 shows a process diagram of another embodiment of the process of this invention in which the natural gas is heated to reaction temperature by electrical energy produced by hydrogen and acetylene is reacted to ethylene prior to liquefaction.

In still another embodiment, as shown in FIGS. 2, 3, and 6, quench outlet stream 19 may be directed to hydrogenation reactor 310, where alkynes, primarily acetylene, may be converted into the preferred intermediate product, ethylene and other olefins, according to general reaction (wherein the alkyne is acetylene):

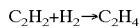

Traditional catalysts for conversion of alkynes to alkenes are used to convert acetylene to ethylene. These include nickel-boride, metallic palladium, and bimetallic catalysts such as palladium with a group 1b metal (copper, silver or gold). Some natural gas feed streams contained trace amounts of sulfur compounds that may act as a poison for the hydrogenation catalyst. In addition, incoming sulfur compounds may react in the hydrogen combustion furnace to form catalyst poisons, such as COS and $H_2S$. It is preferable to remove or reduce the concentration of these catalyst poisons by means well known by those in the art, such as activated carbon or amine.

The products of the reaction that occurs in hydrogenation reactor 310 are conveyed to hydrogen separator 20 through hydrogenation outlet stream 312. Because the conversion from acetylene to ethylene is not complete, hydrogenation outlet stream 312 contains both acetylene and ethylene, as well as hydrogen and some higher-molecular-weight alkynes and alkenes. In alternative embodiments, after leaving high temperature reactor 110 in FIG. 3 or hydrogen combustion furnace 210 in FIG. 4, furnace outlet stream 18 may be directed to hydrogen separator 20, bypassing hydrogenation reactor 310.

Figure 4:
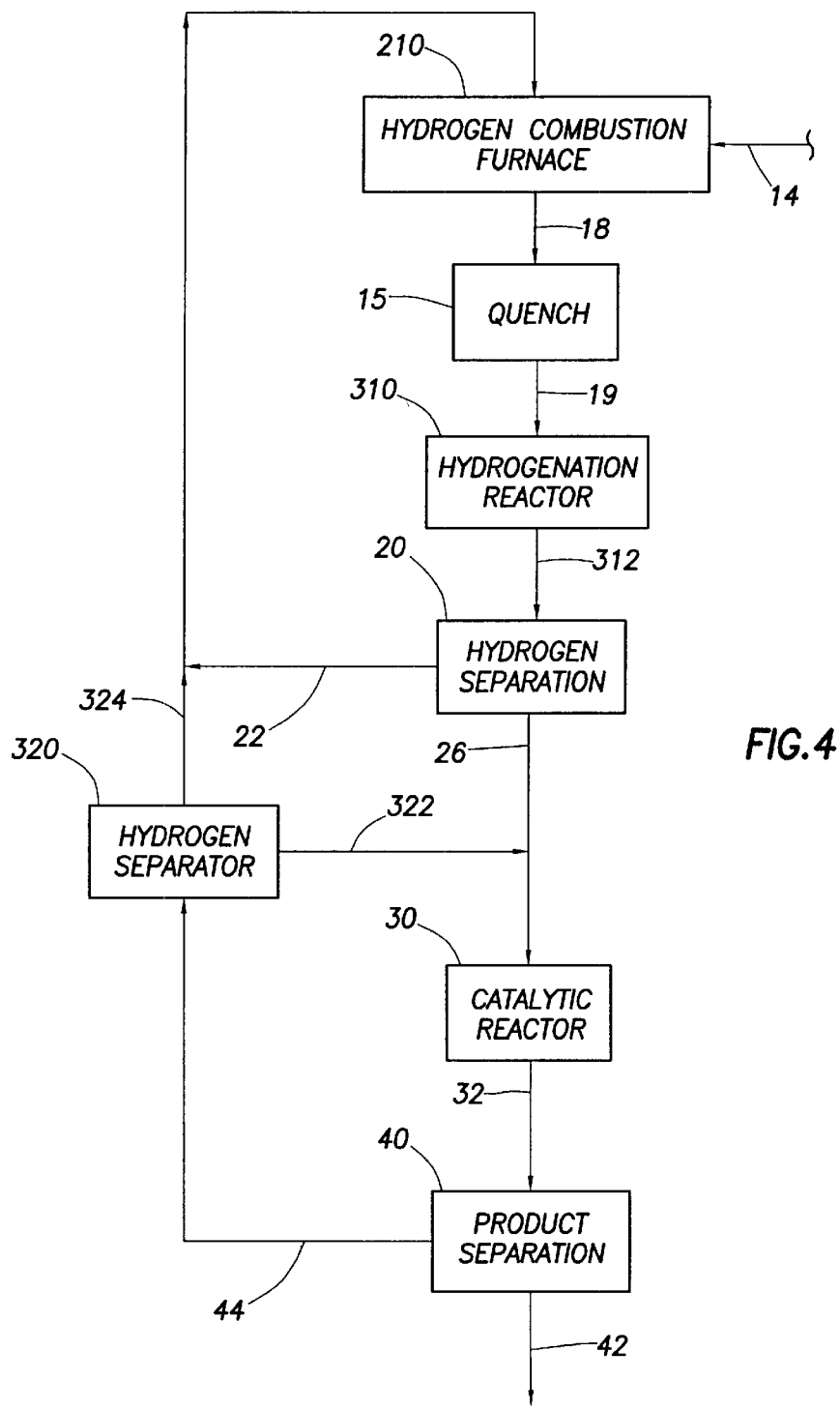
FIG. 4 shows a process diagram for one embodiment of the process of this invention in which the natural gas is heated to reaction temperature by burning some of the natural gas in a furnace and acetylene is reacted to ethylene prior to liquefaction.

In another alternate embodiment also shown in FIGS. 2, 3, and 4, light gas recycle stream 44 may be routed to secondary hydrogen separator 320. Like hydrogen separator 20, this separation step may be performed by any of a variety of processes, including membrane or pressure swing processes, described for example in: A. Malek and S. Farooq, "Hydrogen Purification from Refinery Fuel Gas by Pressure Swing Adsorption". *AIChE J.* 44, 1985 (1998). As shown in FIG. 2, hydrogen removed during separation in secondary hydrogen separator 320 is removed through secondary hydrogen separator hydrogen stream 324. A portion of secondary hydrogen separator hydrogen stream 324 may be routed to electrical generator 50 through recycle purge stream 46. The remaining components of light gas recycle stream 44 exit secondary hydrogen separator 320 through secondary hydrogen separator outlet stream 322. A portion of secondary hydrogen separator outlet stream may be sent to electrical generator 50 through secondary hydrogen separator purge stream 328. The remainder of hydrogen separator outlet stream 322 may be routed to the inlet of catalytic reactor 30 through hydrogen separator recycle stream 326. In another embodiment as shown in FIG. 3, secondary hydrogen separator hydrogen stream 324 is combined with hydrogen separator hydrogen stream 22 and sent to electrical generator 50. Secondary hydrogen separator outlet stream 322 is sent to the inlet of catalytic reactor 30. In another embodiment, shown in FIG. 4, secondary hydrogen separator hydrogen stream 324 is combined with hydrogen separator hydrogen stream 22 and sent to hydrogen combustion furnace 210. In FIG. 6, still another embodiment is shown where secondary hydrogen separator hydrogen stream is combined with hydrogen separator hydrogen stream 22 to maximize production of hydrogen. Secondary hydrogen separator 320 may be used in lieu, instead of in addition to, hydrogen separator 20. Catalytic reactor outlet stream 32 may also be directed to product separation 40 without the use of secondary hydrogen separator 320, as shown in FIG. 1.

Although the present invention has been described with reference to specific details, it is not intended that such details should be regarded as limitations upon the scope of the invention, except as and to the extent that they are included in the accompanying claims.

What we claim is:

1. A method for converting natural gas to a hydrocarbon liquid and water, comprising the steps of:
   a) providing a stream of natural gas;
   b) separating the natural gas stream into a feed stream and a burn stream;
   c) conveying the feed stream and burn stream to a furnace wherein the burn stream is burned and wherein the feed stream is heated to form hydrogen and reactive products comprising an acetylene portion;
   d) quenching the reactive products and hydrogen;
   e) separating the reactive products and hydrogen;
   f) conveying the reactive products to a catalytic liquefaction reactor and providing natural gas and a catalyst in the reactor such that the reactive products and natural gas react to produce hydrogen and the hydrocarbon liquid; and
   g) conveying the hydrocarbon liquid storage or transport.

2. The method of claim 1 wherein the pressure of the natural gas stream is between about 1 bar and about 20 bars.

3. The method of claim 1 wherein in step b) the feed stream is heated to a temperature in the range from about 1000 K to about 1800 K.

4. The method of claim 3 wherein the feed stream is maintained at a temperature of at least 1000 K for less than 100 milliseconds.

5. The method of claim 4 wherein the feed stream is maintained at a temperature of at least 1000 K for less than 80 milliseconds.

6. The method of claim 1 wherein the catalyst in the catalytic liquefaction reactor is an acid catalyst.

7. The method of claim 1 wherein the temperature in the catalytic liquefaction reactor is in the range from about 300 K to about 1000 K.

8. The method of claim 1 wherein the burn stream is burned using oxygen-enriched air.

9. The method of claim 1 further comprising after step e)

h) conveying the hydrogen to a fuel cell or turbine;

i) providing oxygen to the fuel cell or turbine;

j) reacting the hydrogen with the oxygen in the fuel cell or burning the hydrogen with the oxygen in the turbine to produce electricity.

10. The method of claim 9 wherein the fuel cell or turbine produce heat.

11. The method of claim 10 further comprising after step j):

k) heating water produced in the fuel cell or turbine with heat produced in the fuel cell to form steam and;

l) generating electricity from the steam.

12. The method of claim 1 wherein the step of quenching is performed by a Joule-Thompson expander, nozzle or turbo expander.

13. The method of claim 1 further comprising prior to step e) but after step d):

conveying the reactive products and hydrogen to a hydrogenation reactor and reacting the acetylene portion of the reactive products with the hydrogen to form ethylene.

14. The method of claim 1 further comprising after step f):

separating the hydrogen from the hydrocarbon liquid;

providing oxygen to the a cell or turbine; and reacting the hydrogen with the oxygen in the fuel cell or burning the hydrogen with the oxygen in the turbine to produce electricity.

15. The method of claim 1, wherein the hydrocarbon liquid comprises naphtha or gasoline.

16. The method of claim 1 further comprising after step b) but before step c):

segregating of portion of the feed stream to form an electrical generation stream;

conveying the electrical generation stream to a fuel cell or turbine;

providing oxygen to their fuel cell or turbine;

reacting the electrical generation stream with the oxygen in the fuel cell or burning the electrical generation stream with the oxygen in the turbine to form electricity.

17. A method for converting natural gas to a hydrocarbon liquid and water, comprising the steps of:

a) providing a stream of natural gas;

b) conveying the natural gas to a reactor having means for heating the natural gas using electrical power, wherein the natural gas is heated to form hydrogen and reactive products comprising an acetylene portion;

c) quenching the reactive products and hydrogen;

d) conveying the reactive products and hydrogen to a hydrogenation reactor;

e) reacting the acetylene portion of the reactive products with hydrogen to form ethylene;

f) conveying the reactive products to a catalytic liquefaction reactor and providing natural gas and a catalyst in the liquefaction reactor such that the reactive products and natural gas react to produce hydrogen and the hydrocarbon liquid;

g) conveying hydrogen to a means for generating electrical power and producing water;

h) conveying the electrical power from the means for generating electrical power to the reactor having means for heating using electrical power;

i) conveying the hydrocarbon liquid and the water to storage or transport.

18. The method of claim 17 wherein in step b) the means for heating the natural gas using electrical power is an electric arc, resistance heating a plasma reactor, a fuel cell, or a combined cycle gas turbine drive electrical generator.

19. The method of claim 17 wherein the selected pressure of the natural gas stream is between about 1 bar and about 12 bars.

20. The method of claim 17 wherein in step b) the natural gas is heated to a temperature in the range from about 1000 K to about 1800 K.

21. The method of claim 17 wherein the feed stream is maintained at a temperature of at lest 1000 K for less than 100 milliseconds.

22. The method of claim 21 wherein the natural gas stream is maintained at a temperature of at least 1000 K for less than 100 milliseconds.

23. The method of claim 22 wherein the natural gas stream is maintained at a temperature of at least 1000 K for less than 80 milliseconds.

24. The method of claim 17 wherein the catalyst in the catalytic liquefaction reactor is an acid catalyst.

25. The method of claim 17 wherein the temperature in the catalytic liquefaction reactor is in the range from about 300 K to about 1000 K.

26. The method of claim 17 wherein the step of quenching is performed by a Joule-Thompson expander, nozzle or turbo expander.

27. The method of claim 17 further comprising after step a) but before step b)

segregating a portion of the natural gas stream to form an electrical generation stream;

conveying the electrical generation stream to a fuel cell or turbine;

conveying the hydrogen to a means for generating electrical power and producing water.

28. A method for converting natural gas to a hydrocarbon liquid and water, comprising the steps of:

a) providing a stream of natural gas;

b) conveying the natural gas through a furnace wherein hydrogen is burned and wherein the natural gas is heated to form hydrogen and reactive products, comprising an acetylene portion;

c) quenching the reactive products and hydrogen;

d) conveying the reactive products and hydrogen to a hydrogenation reactor;

e) reacting the acetylene portion of the reactive products with hydrogen to form ethylene;

f) conveying the reactive products and hydrogen to a catalytic liquefaction reactor and providing natural gas and a catalyst in the reactor such that the reactive products and natural gas react to produce hydrogen and the hydrocarbon liquid;

g) conveying hydrogen from the catalytic liquefaction reactor to the hydrogen furnace for burning so as to heat the natural gas and produce water; and h) conveying the hydrocarbon liquid and the water to storage or transport.

29. The method of claim 28 wherein the selected pressure of the natural gas stream is between about 1 bar and about 12 bars.

30. The method of claim 28 wherein in step b) the natural gas is heated to a temperature in the range from about 1000 K to about 1800 K.

31. The method of claim 30 wherein the natural gas stream is maintained at a temperature of at least 1000 K for less than 100 milliseconds.

32. The method of claim 31 wherein the natural gas stream is maintained at a temperature of at least 1000 K for less than 80 milliseconds.

33. The method of claim 28 wherein the catalyst in the catalytic liquefaction reactor is an acid catalyst.

34. The method of claim 28 wherein the temperature in the catalytic liquefaction reactor is in the range from about 300 K to about 1000 K.

35. The method of claim 28 wherein the hydrogen is burned using oxygen-enriched air.

36. The method of claim 28 wherein the step of quenching is performed by a Joule-Thompson expander, nozzle or turbo expander.

37. A method for converting natural gas to naphtha or gasoline and water, comprising the steps of:
    a) providing a stream of natural gas;
    b) conveying the natural gas to reactor having means for heating the natural gas using electrical power, wherein the natural gas is heated to form hydrogen and reactive products comprising an acetylene portion;
    c) quenching the reactive products and hydrogen;
    d) conveying the reactive products and hydrogen to a hydrogenation reactor;
    e) reacting the acetylene portion of the reactive products with hydrogen to form ethylene;
    f) conveying the reactive product stream to a catalytic liquefaction reactor and providing natural gas and a catalyst in the liquefaction reactor such that the reactive products and natural gas react to produce hydrogen and naphtha or gasoline;
    g) conveying the hydrogen to a means for generating electrical power and producing water;
    h) conveying the electrical power to the reactor having means for heating using electrical power; and
    i) conveying the naphtha or gasoline and the water to storage or transport.

38. The method of claim 36 wherein the selected pressure of the natural gas stream is between about 1 bar and about 12 bars.

39. The method of claim 36 wherein in step b) the natural gas is heated to a temperature in the range from about 1000 K to about 1800 K.

40. The method of claim 39 wherein the natural gas stream is maintained at a temperature of at least 1000 K for less than 100 milliseconds.

41. The method of claim 40 wherein the natural gas stream is maintained at a temperature of at least 1000 K for less than 80 milliseconds.

42. The method of claim 37 wherein the catalyst in the catalytic liquefaction reactor is an acid catalyst.

43. The method of claim 37 wherein the temperature in the catalytic liquefaction reactor is in the range from about 300 K to 1000 K.

44. The method of claim 37 wherein the hydrogen is burned using oxygen enriched air.

45. The method of claim 37 wherein the step of quenching is performed by a Joule-Thompson expander, nozzle or turbo expander.

46. A method for converting natural gas to naphtha or gasoline and water, comprising the steps of:
    a) providing a stream of natural gas;
    b) conveying the natural gas through a furnace wherein hydrogen is burned and wherein the natural gas is heated to form hydrogen and reactive products, comprising an acetylene portion;
    c) quenching the reactive products and hydrogen;
    d) conveying the reactive products and hydrogen to a hydrogenation reactor;
    e) reacting the acetylene portion of the reactive products with hydrogen to form ethylene;
    f) conveying the reactive products and hydrogen to a catalytic liquefaction reactor and providing natural gas and a catalyst in the reactor such that the reactive products and natural gas react to produce hydrogen and naphtha or gasoline;
    g) conveying hydrogen from the catalytic liquefaction reactor to the hydrogen furnace for burning so as to heat the natural gas and produce water; and
    h) conveying the naphtha or gasoline and the water to storage or transport.

47. The method of claim 46 wherein the selected pressure of the natural gas stream is between about 1 bar and about 12 bars.

48. The method of claim 46 wherein in step b) the natural gas is heated to a temperature in the range from about 1000 K to about 1800 K.

49. The method of claim 48 wherein the natural gas stream is maintained at a temperature of at least 1000 K for less than 100 milliseconds.

50. The method of claim 49 wherein the natural gas stream is maintained at a temperature of at least 1000 K for less than 80 milliseconds.

51. The method of claim 46 wherein the catalyst in the catalytic liquefaction reactor is an acid catalyst.

52. The method of claim 46 wherein the temperature in the catalytic liquefaction reactor is in the range from about 300 K to 1000 K.

53. The method of claim 46 wherein the hydrogen is burned using oxygen enriched air.

54. The method of claim 46 wherein the step of quenching is performed by a Joule-Thompson expander, nozzle or turbo expander.

* * * * *

UNITED STATES PATENT AND TRADEMARK OFFICE
CERTIFICATE OF CORRECTION

PATENT NO. : 6,602,920 B2 Page 1 of 1
DATED : August 5, 2003
INVENTOR(S) : Kenneth R. Hall et al.

It is certified that error appears in the above-identified patent and that said Letters Patent is hereby corrected as shown below:

<u>Column 7,</u>
Line 60, after "Adsorption", delete "." and insert -- , --.

Signed and Sealed this

Thirteenth Day of January, 2004

JON W. DUDAS
*Acting Director of the United States Patent and Trademark Office*